United States Patent
Seifert (10) Patent No.: US 9,489,733 B2
(45) Date of Patent: Nov. 8, 2016

(54) QUERY-SPECIFIC GENERATION AND RETRIEVAL OF MEDICAL VOLUME IMAGES

(71) Applicant: Siemens Aktiengesellschaft, Munich (DE)

(72) Inventor: Sascha Seifert, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 128 days.

(21) Appl. No.: 14/493,490

(22) Filed: Sep. 23, 2014

(65) Prior Publication Data
US 2015/0161786 A1  Jun. 11, 2015

(30) Foreign Application Priority Data
Dec. 6, 2013 (EP) ..................... 13196077

(51) Int. Cl.
*G06K 9/36* (2006.01)
*G06T 7/00* (2006.01)
*A61B 6/00* (2006.01)
*G06F 17/30* (2006.01)
*G06K 9/00* (2006.01)
*G06T 17/00* (2006.01)

(52) U.S. Cl.
CPC .......... *G06T 7/0012* (2013.01); *A61B 6/5205* (2013.01); *A61B 6/5211* (2013.01); *G06F 17/3028* (2013.01); *G06K 9/00147* (2013.01); *G06T 7/0089* (2013.01); *G06T 17/00* (2013.01); *G06T 2207/20128* (2013.01); *G06T 2207/30004* (2013.01)

(58) Field of Classification Search
None
See application file for complete search history.

(56) References Cited

U.S. PATENT DOCUMENTS

| 2011/0142320 A1* | 6/2011 | Gupta | G06F 19/321 382/131 |
| 2015/0131882 A1* | 5/2015 | Mohr | G06T 7/0081 382/131 |

OTHER PUBLICATIONS

Rohr et al.; Landmark-Based Elastic Registration Using Approximating Thin-Plate Splines, in: IEEE Transactions on Medical Imaging, vol. 20, No. 6, Jun. 2001, pp. 526-534; Jun. 1, 2001.
Manuel Möller et al: "RadSem: Semantic Annotation and Retrieval for Medical Images", May 31, 2009, The Semantic Web: Research and Applications, Springer Berlin Heidelberg, Berlin, Heidelberg, pp. 21-35.
Hierarchical Parsing and Semantic Navigation of Full Body CT Data, SPIE 2009 S. Seifert, A. Barbu, S. Zhou, D. Liu, J. Feulner, M. Huber, M. Suehling, A. Cavallero, D. Comaniciu.
B. Michael Kelm et al: Spine detection in CT and MR using iterated marginal space learning, Medical Image Analysis 17 (2013), pp. 1283-1292,; 2013.

(Continued)

*Primary Examiner* — Brian P Werner
(74) *Attorney, Agent, or Firm* — Harness, Dickey & Pierce P.L.C.

(57) ABSTRACT

Methods and a system are disclosed for providing a mechanism for searching and extracting three-dimensional regions of interest in image archives. In at least one embodiment, a textual search query serves as input and is processed in order to provide a newly generated query-specific volume image, including computed sub-volumes covering the anatomical structure the query refers to. The query is input via a graphical search interface and the sub-volumes are outputted also via the graphical search interface.

20 Claims, 5 Drawing Sheets

(56) References Cited

OTHER PUBLICATIONS

Matthias Dorfer et al.: Constructing an Un-biased Whole Body Atlas from Clinical Imaging Data by Fragment Bundling, MICCAI 2013, Part I, LNCS 8149, pp. 219-226, Springer-Verlag Berlin Heidelberg 2013.

Sascha Seifert et al.: Semantic Annotation of Medical Images, Medical Imaging 2010. Proc. of SPIE vol. 7628; 2010.

Seifert Sascha et al; "Combined Semantic and Similarity Search in Medical Image Databases"; Medical Imaging 2011; vol. 7967; No. 1; pp. 1-10; DOI: 10.1117/12.878179: XP060009610; 2011: Mar. 3, 2011.

http://bioportal.org.

http://www.yottalook.com.

http://goldminer.arrs.org.

Extended European Search Report dated Apr. 22, 2014.

Diaz-Galiano M.C. et al.: "Query expansion with a medical ontology to improve a multimoldal information retrieval system"; Computers in Biology and Medicine, New York, NY, US; vol. 39; No. 4; pp. 396-403; XP026072609; ISSN:0010-4825, 001: 10.1016/J.COMPBIOMED.2009.01.012 (Mar. 6, 2009).

Office Action dated Feb. 19, 2016 in European Application No. 13 196 077.5.

* cited by examiner

QUERY-SPECIFIC GENERATION AND RETRIEVAL OF MEDICAL VOLUME IMAGES

PRIORITY STATEMENT

The present application hereby claims priority under 35 U.S.C. §119 to European patent application number EP 131960775 filed Dec. 6, 2013, the entire contents of which are hereby incorporated herein by reference.

FIELD

The present invention generally relates to the fields of medical imaging and data processing and in particular relates to a query-based semantic full body region of interest extraction in a plurality of medical images.

For the purpose of medical diagnosis and also for scientific issues it is necessary to view and analyze medical images. Image-based medicine has applications inter alia in radiology, cardiology and surgery. Today, medical diagnosis is mainly based on medical images. Particularly, in evidence-based medicine there is an immense need for tools, supporting the physician in validating his diagnosis. One means of validating is to compare the medical images from a current patient with other reference images from other patients or from images of the same patient at other acquisition times, which are stored in an image database (for example PACS, PACS: picture archiving and communications system). Also, other libraries may be accessible in the internet. The kind of images is not restricted, so that two-dimensional images and three-dimensional images from different acquisition modalities have to be considered (for example computer tomography/CT, magnetic resonance tomography/MRT, tomosynthesis images etc.).

BACKGROUND

On the internet there are already several search engines for medical images available, such as Yotta or Goldminer, which enable the user to search for images given a keyword. The images or their reference are entered into the system by web crawling or uploading by publishers and users. Subsequently, these images are manually tagged by users or by a heuristic considering the context information at the web site where the image was found. Unfortunately, the automatic approach cannot be that precise as needed for validating diagnosis because of a lack of real understanding of the image. Hence, the system also cannot provide automatic zoom into or navigation to the image location visualizing only the queried anatomical structure.

Another disadvantage is that the user has to load the whole image and scroll to the desired image location, the region of interest (ROI), which is very time-consuming, especially if the user wants to compare ROI from hundreds of patients. In this respect the huge progress in medical image acquisition in the last decade has to be mentioned, which led to images of gigabyte size acquired within seconds, and the trend towards larger images is still ongoing, which has immense impact on image loading time.

As an example, the user wants to find medical images which only show the heart without disturbing image region which draw off attention and then display in parallel with images from several other patients in a gallery, the images need to be adequately shrunken to the ROI to fit on the screen and enable easy comparison by the user.

Another major aspect and disadvantage of known systems is the lack of semantic understanding of the query string itself in current systems. What would be beneficial is that the system works semantically such that a query can be automatically expanded into meaningful related sub-queries to increase recall, e.g., given the heart, the search should also search for images tagged with narrower terms such as aortic valve or myocardial chambers, which are both components of the heart.

Developing new image processing algorithms in industry or academia need to train or evaluate against a huge set of image examples. It is a very time-consuming and incomplete task to find all images showing an adequate ROI needed for the algorithm development. The situation today is that the researcher manually inspects images in a database, crops the relevant part and stores them in his own developer database. There is a huge trend towards trained image algorithms by the use of statistical models coming from machine learning. These algorithms are used to build software detectors which automatically localize an object in a medical image. This approach requires that positive and negative examples are presented to a training algorithm, i.e. image regions showing and explicitly not showing the object which should be learned. Today this is all hand work.

In state of the art systems in medicine users cannot retrieve images from a database shrunken to that part of the image showing the anatomical structure of interest. They have to load the whole image and scroll to that location or crop the ROI by hand. This is extremely time-consuming and impossible if hundreds of patients for a given anatomical structure should be compared in parallel.

Even at the beginning, when the user inputs a query string into a search engine, the system does not really understand what is meant; it just compares texts with patterns. This makes it impossible to expand the query to meaningful, related queries which are from the medical point of view also relevant, e.g., as another example what the user wants: querying for images showing the abdomen should result in images tagged with anatomical structures located in the abdomen such as the liver, the pancreas, the intestine, etc. (these are hundreds or even thousands of items)

The developer of an image processing algorithm needs to crop and label ROI by hand to correctly present the data to a training algorithm. This is a very time-consuming task and must always be redone for every new anatomical structure where such an object detector should be developed.

There is no other solution today than manually checking every medical image in the database, loading the image and cropping the relevant parts. This procedure is extremely time-consuming. Query strings must be expressed with care to match the tags in the database and must be manually expanded into meaningful sub-queries to increase the search precision and recall.

SUMMARY

At least one embodiment of the invention is directed to a computer implemented tool which enables the user to get all the relevant three-dimensional medical images on one click in response to his query. The query relates to a specific anatomical structure (for example the liver, heart, kidney etc.) and the purpose is that he gets a composition of three-dimensional images which has been selected from a plurality of three-dimensional images (from different patients and/or from different acquisition times and/or acquisition modalities) and which all do comprise the relevant anatomical structure, the query refers to. Thus, it should no longer be necessary that the user manually clicks through the set of plurality of three-dimensional images, stored in an image archive in order to select the relevant images and subsequently to load these images and to again select the relevant part of the respective images, which is necessary for answering the respective query. All these steps, mentioned before, should be automated.

As an example: If the user inputs a query: "show images of livers with liver tumors", then, the system should automatically parse this query and start a search in the database for images relating to (possibly: different) liver tumors. However, in order to provide the user only with relevant image information, it is necessary that only the liver-related parts of the images and tumor related images are to be considered. Further, it is necessary that a plurality of three-dimensional images is considered (for example from different patients and/or from the same patients at different acquisition times etc.). Accordingly, the system should provide a query-specific new image, covering the related anatomical structure (here: the liver tumor) and to merge these three-dimensional volume images to one common volume image.

At least one embodiment of the present invention resolves at least one of the above mentioned problems. To this end, and an automatic image processing method is provided in at least one embodiment. The image preprocessing method serves to generate sub-volumes of a plurality of three-dimensional medical volumes for the purpose of semantic extraction of anatomical structures in different three-dimensional medical volumes. The method comprises:

providing or acquiring and reconstructing a medical three-dimensional image, which is referred to as volume or image volume and which may contain different anatomical structures (or one structure) or may consist of at least a part of an anatomical structure
   automatically detecting landmarks in the volume
   automatically matching the detected landmarks with at least one atlas image to generate an indexed volume
   automatically splitting the indexed volume into indexed sub-volumes according to index data and/or atlas image data, which may be stored in an atlas image database
   storing the indexed sub-volumes in a database for retrieval of anatomical structures or for other processings.

According to a further aspect, at least one embodiment of the present invention refers to a method for query-based extraction of anatomical structures in a plurality of three-dimensional medical images. The method comprises:

providing (or acquiring and reconstructing) a plurality of medical volumes with sub-volumes, which are preprocessed and indexed according to the automatic image preprocessing method, mentioned above (and referred to in claim 1) and wherein the medical volumes do comprise at least an anatomical structure (usually more than one) or a part of an anatomical structure
   feeding in (input) and parsing a textual medical query, referring to an anatomical structure
   automatically mapping the parsed query to at least one ontological data entry in an ontology database by way of a meta image index
   automatically computing a set of sub-volumes which have an index which matches the query, wherein the set of sub-volumes consists of at least a part of the anatomical structure which the query refers to
   automatically merging the set of computed sub-volumes to generate a query-specific volume
   displaying the query-specific volume.

According to another aspect, at least one embodiment of the present invention refers to a system for feature-based extraction of medical sub-volumes within a plurality of volumes. The system comprises an image archive, a workflow unit, a landmark detector unit, a registration unit, a split and merge unit, a knowledge repository, a graphical search interface, a search engine and a sub-volume selector.

According to another aspect of at least one embodiment of the present invention, a computer program product, stored on a computer readable medium, comprises software code sections, wherein the software code sections are adapted to execute the method according to at least one embodiment of the method (the method for automatic image preprocessing) and/or at least another embodiment of the method (the method for query-based extraction of anatomical structures), if the software code sections are executed or loaded on a computer.

According to another aspect, at least one embodiment of the invention further refers to a computer program for executing the method according to at least one embodiment of the invention.

It has to be pointed out that any of the aforementioned embodiments of the methods may be embodied in the form of a computer program. The computer program may be stored on a computer readable media and is adapted to perform any of the aforementioned methods when run on a computer device, a network of computer devices or on a processor in a computing device (such as a handheld or a mobile phone). Thus, the storage medium or computer readable medium, is adapted to store information and is adapted to interact with a data processing facility or a computing device to perform the method of any of the above mentioned embodiments. The storage medium may be a build-in medium installed inside a computer device's main body or a removable medium arranged so that it can be separated from the computer device's main body. Examples of the build-in medium include, but are not limited to, re-writable non-volatile memories, such as ROMs and flash memories and hard disks. Examples of the removable medium include, but are not limited to, optical storage media such as CD-ROMs and DVD's; magneto-optical storage media such as MOs magnetism storage media such as floppy discs, cassette tapes, removable hard disks, memory cards etc.

In general, at least one embodiment of the invention refers to a computer-based implementation of a query-specific generation of medical volumes and to an automatic retrieval of volume sections to which a query refers to. A major advantage of at least one embodiment of the invention is that the method may be used for automatically localizing anatomical structures in a plurality of medical volumes without loading each of the volume images separately and manually searching the anatomical structure in the volume. The method automatically aggregates all the different relevant volume images and extracts the relevant structures in it (the regions of interest, the query refers to) and aggregates these relevant structures in the plurality of different images to a common query-specific volume image.

According to another aspect, at least one embodiment of the invention may be implemented in a computer program being loadable in a memory of a computer, wherein the computer program is adapted to carry out the steps of at least one embodiment of the methods as mentioned above.

DETAILED DESCRIPTION OF THE EXAMPLE EMBODIMENTS

The figures illustrate principles of the invention according to specific embodiments. Thus, it is also possible to implement the invention in other embodiments, so that these figures are only to be construed as examples. Moreover, in the figures, like reference numerals designate corresponding modules or items throughout the different drawings.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the present invention resolves at least one of the above mentioned problems. To this end, and an automatic image processing method is provided in at least one embodiment. The image preprocessing method serves to generate sub-volumes of a plurality of three-dimensional medical volumes for the purpose of semantic extraction of anatomical structures in different three-dimensional medical volumes. The method comprises:

providing or acquiring and reconstructing a medical three-dimensional image, which is referred to as volume or image volume and which may contain different anatomical structures (or one structure) or may consist of at least a part of an anatomical structure automatically detecting landmarks in the volume automatically matching the detected landmarks with at least one atlas image to generate an indexed volume automatically splitting the indexed volume into indexed sub-volumes according to index data and/or atlas image data, which may be stored in an atlas image database storing the indexed sub-volumes in a database for retrieval of anatomical structures or for other processings.

According to a further aspect, at least one embodiment of the present invention refers to a method for query-based extraction of anatomical structures in a plurality of three-dimensional medical images. The method comprises:

providing (or acquiring and reconstructing) a plurality of medical volumes with sub-volumes, which are preprocessed and indexed according to the automatic image preprocessing method, mentioned above (and referred to in claim 1) and wherein the medical volumes do comprise at least an anatomical structure (usually more than one) or a part of an anatomical structure feeding in (input) and parsing a textual medical query, referring to an anatomical structure automatically mapping the parsed query to at least one ontological data entry in an ontology database by way of a meta image index automatically computing a set of sub-volumes which have an index which matches the query, wherein the set of sub-volumes consists of at least a part of the anatomical structure which the query refers to automatically merging the set of computed sub-volumes to generate a query-specific volume displaying the query-specific volume.

According to another aspect, at least one embodiment of the present invention refers to a system for feature-based extraction of medical sub-volumes within a plurality of volumes. The system comprises an image archive, a workflow unit, a landmark detector unit, a registration unit, a split and merge unit, a knowledge repository, a graphical search interface, a search engine and a sub-volume selector.

In an advantageous embodiment the system may further comprise an additional sub-volume archive for storing the indexed sub-volumes. Further, the system may comprise of a query expansion unit which is adapted to expand the input query to anatomical features by accessing the background knowledge database.

According to another aspect of at least one embodiment of the present invention, a computer program product, stored on a computer readable medium, comprises software code sections, wherein the software code sections are adapted to execute the method according to at least one embodiment of the method (the method for automatic image preprocessing) and/or at least another embodiment of the method (the method for query-based extraction of anatomical structures), if the software code sections are executed or loaded on a computer.

According to another aspect, at least one embodiment of the invention further refers to a computer program for executing the method according to at least one embodiment of the invention.

It has to be pointed out that any of the aforementioned embodiments of the methods may be embodied in the form of a computer program. The computer program may be stored on a computer readable media and is adapted to perform any of the aforementioned methods when run on a computer device, a network of computer devices or on a processor in a computing device (such as a handheld or a mobile phone). Thus, the storage medium or computer readable medium, is adapted to store information and is adapted to interact with a data processing facility or a computing device to perform the method of any of the above mentioned embodiments. The storage medium may be a build-in medium installed inside a computer device's main body or a removable medium arranged so that it can be separated from the computer device's main body. Examples of the build-in medium include, but are not limited to, re-writable non-volatile memories, such as ROMs and flash memories and hard disks. Examples of the removable medium include, but are not limited to, optical storage media such as CD-ROMs and DVD's; magneto-optical storage media such as MOs magnetism storage media such as floppy discs, cassette tapes, removable hard disks, memory cards etc.

In general, at least one embodiment of the invention refers to a computer-based implementation of a query-specific generation of medical volumes and to an automatic retrieval of volume sections to which a query refers to. A major advantage of at least one embodiment of the invention is that the method may be used for automatically localizing anatomical structures in a plurality of medical volumes without loading each of the volume images separately and manually searching the anatomical structure in the volume. The method automatically aggregates all the different relevant volume images and extracts the relevant structures in it (the regions of interest, the query refers to) and aggregates these relevant structures in the plurality of different images to a common query-specific volume image.

In the following, there is given a short explication and definition of terms, used in this disclosure.

The term "volume" refers to a medical volume, i.e. a reconstructed three-dimensional image of a part of a patient's body, for example three-dimensional image of the heart, the liver, the kidneys etc. The volume may be acquired by a respective acquisition device (for example magnetic resonance apparatuses, X-ray devices, like tomosynthesis apparatuses, computer tomography systems, PET devices, ultra sound devices etc.). Typically, the three-dimensional volumes are reconstructed from a set of two-dimensional images. It is also possible to access a database, in which the three-dimensional volumes are already stored (because they have been acquired at an earlier stage). Typically, several medical volumes may be related to one single patient. For example the same anatomical structure of the same patient may be examined on several points in times or different anatomical structures of the patient may be examined and imaged in order to generate the medical volume. Further, a plurality of medical volumes of different patients is to be considered for at least one embodiment of the image pre-processing method and as well as for at least one embodiment of the query-based extraction method according to pending claims.

The term "sub-volume" refers to a part or portion of a medical image volume. A sub-volume is a three-dimensional medical image, for example a cube with a specific edge length, for example, typically, 5 cm (for example for bigger organs). The form and/or the dimensions of the sub-volume is/are configurable in a preparation phase. According to a preferred embodiment, it is also possible to add an automatic selector, which may be implemented as a selection algorithm which has the functionality to select an appropriate size and form of the sub-volumes according to (and, thus, in dependence of) the organ to be queried. Further, also other forms, for example a cuboid may be generated as well so that the segmentation of the volume in sub-volumes does not necessarily be a equidistant or equally spaced segmentation but could be a segmentation according to the structure, position and form of the respective organ or anatomical structure. The anatomical structure may refer to a patient's feature, like a specific bone, or a specific organ or a part of a patient's object (including vessels), like a part of the kidney, for example kidney parenchyma. The anatomical structure may be referred to as feature or as region of interest, too.

According to at least one embodiment of the present invention, landmarks are automatically detected in the three-dimensional volume. Preferably, this is executed by way of algorithms which are used to build software detectors which automatically localize an object in a medical (three-dimensional) image. The landmark-based detection approach may be executed according to known state of the art landmark-based registration methods, for example described in "Landmark-based elastic registration using approximating thin-plate splines" (K. Rohr, H. S. Stiehl, R. Sprengel, T. M. Buzug, J. Weese, and M. Kuhn, "Landmark-based elastic registration using approximating thin-plate splines", Medical Imaging, IEEE Transactions on, vol. 20, no. 6. IEEE, pp. 526-534, 2001.), the entire contents of each of which is hereby incorporated herein by reference.

According to at least one embodiment, the term "landmark" may refer to anatomical landmarks, in particular, the trachea, sternum and spine etc. However, it is also possible to refer to other kinds of landmarks, like position landmarks and the like. Typically, around 20 landmarks are sufficient for a good quality of image preprocessing. It has to be made sure that sufficient representative landmarks in every body part or portion are present (for example landmarks for the head, the neck, the thorax, abdomen, pelvis and extremities). According to an example embodiment, a background knowledge database is used to automatically decode and understand the anatomical meaning of the respective landmarks detected by the landmark detector unit. The detected landmarks are stored in the meta image index.

According to an example embodiment, the step of "detecting landmarks" is executed iteratively by way of accessing a background knowledge database in order to generate further landmarks by using the detected landmarks as anchor structure. Thus already generated or detected landmarks may be expanded for further landmarks.

The result of the landmark detection is taken and registered or matched with an atlas image. The atlas image is a reference image with reference landmarks. The atlas image may refer to a region of interest in a three-dimensional medical image. The atlas image may be generated by statistical methods which compute an atlas image on the basis of several different images of different patients. Thus, the atlas image may refer to a superposition or interference of a plurality of medical images. According to a preferred embodiment, an automatic processing is used for generating a labeled atlas image database. For example the method described in more detail in the paper below may be applied: M. Dorfer, R. Donner, and G. Langs, "Constructing an Unbiased Whole Body Atlas from Clinical Imaging Data by Fragment Bundling," in Medical Image Computing and Computer-Assisted Intervention-MICCAI 2013, Springer, 2013, pp. 219-226, the entire contents of which are hereby incorporated herein by reference. The reference landmarks have to be generated manually or have to be generated in each of the images separately for later aggregation (superposition).

According to an example embodiment, the at least on atlas image is a multiple atlas image and the step of matching comprises a step of selecting a conforming atlas image from a plurality of different atlas images, which best correspond to the acquired or reconstructed medical three dimensional image. This has the advantage that different atlas images may be used and processed for different patients (female/male, adults/children, small/big patients etc.).

According to an example embodiment, multiple atlas images may be used, which each are referring to different objects, like atlas images for female/male persons, for small/large/tall patients, for children/adults, for healthy structures/tumors etc. The atlas image or the multiple atlas image is also annotated or labeled with landmarks, so that it is possible to register the provided medical volume with the atlas feature and the respective landmarks in the volume with the respective landmarks in the atlas image. Thus, there is a mapping between the (new) image and the (reference) atlas image. For enhancing the quality of this matching or registration step, it is possible to use multiple atlas images, as explained above and the best fit according to a minimal distance of pairing landmarks is selected.

The step of matching or registration may be based on automatic algorithms. According to an example embodiment, a popular algorithm is used, in particular the thin-plate splines landmark registration approach. In this respect it is referred to Rohr, Karl, et al. "Landmark-based elastic registration using approximating thin-plate splines." Medical Imaging, IEEE Transactions on 20.6 (2001): 526-534, the entire contents of which are hereby incorporated herein by reference.

After the step of matching, an indexed volume is generated. This means, that the provided medical three-dimensional image is transferred into an annotated image or into a labeled volume with indexed sub-volumes. For example the indexed volume comprises different structures of the anatomical structure to be examined (i.e. the indexed heart with several indexed heart chambers, so that each of the heart chambers may be retrieved via its index separately and uniquely).

Thus, the volume is splitted or segmented into a plurality of indexed sub-volumes. The indexed sub-volumes refer to different anatomical structures. For example there is a sub-volume for the heart and this sub-volume recursively comprises other sub-volumes with heart chambers. Another sub-volume of the heart may refer to the mediastinal valve. The indexed sub-volumes are stored in a database. According to an embodiment, it is possible to extract these sub-volumes which refer to a specific anatomical structure as the sub-volumes are indexed according to their semantic content. Thus, anatomic structures may be clustered according to their anatomical content. Alternatively, a grid may be superimposed over the volume image in order to generate volume cells of equal size. This has the advantage that these volume blocks may be stored in a very efficient manner (as input/output transfer is usually executed in a block manner). By combining different sematic indices it is possible to load, generate and/or retrieve any anatomical structure of a patient's body volume.

"Normalizing" refers to automatically detecting the respective anatomical structure in the provided medical volume. For example in case of a patient's head is depicted in the medical volume, the step of normalizing means that the provided medical head is automatically registered with the atlas image in order to know, which structure is shown in the image. Image registration is the process of systematically placing separate images in a common frame of reference so that the information they contain can be optimally integrated and/or compared. This may be executed by matching the detected landmarks with known landmarks in the atlas image. As a result of normalizing, it is known which part of the patient's body the provided volume or image refers to. For example if the provided image refers to a patient's head, after the step of normalizing the provided image is labeled or annotated with meta information "head" and optionally further localization information may be extracted, in order to show that the image refers to the upper part of the patient.

The term "partitioning" refers to a segmentation or division of the total volume in smaller volume cells. The cells may have equal or different size and/or form. For efficiency reasons (data transmission and storage capacity) cells of same size and form are used. The size of the cells is configurable in a preparation phase, particularly in dependence of the anatomical structure to be extracted and independent of the acquisition parameters and can be specified in units of length, comprising centimeter or millimeter.

A query typically refers to a textual query, for example like "gall stones", "kidney tumors", "heart" etc. it is also possible to input several word strings as query for example like "heart chamber". Further, it is also possible to input a question, e.g.: "give me all regions of interest with the heart". The search engine parses this query input and maps it to semantic index information, i.e. to ontological concepts. Together with index information from a meta image index the concepts are forwarded to another computer-based instance, i.e. to a query expansion unit. The task of the query expansion unit is to expand the input concept into related meaningful concept(s) by use of a background knowledge database. The results are multiple sub-queries.

The ontology database may be embodied by a commercial graph based database such as for example OpenLink Virtuoso™ or Apache Jena. This ontology database contains some open ontologies available at such as the Foundational Model of Anatomy, Radlex or licensed ontologies such as Snomed CT. An example for such an ontology database which describes human anatomy is given in S. Seifert et al., "Semantic annotation of medical images," in SPIE Medical imaging, 2010, pp. 762808-762808, the entire contents of which are hereby incorporated herein by reference.

An aspect of at least one embodiment of the method for query-based extraction of anatomical structures is to be seen in computing a set of sub-volumes which have an index that matches the input query. This means that all the computed sub-volumes consist of at least a part of the anatomical structure which the query refers to. In case the user inputs the string "give me all regions of interest of the heart", the computed set of sub-volumes all refer to three-dimensional anatomical structures of the heart, like left/right, upper/lower atrium with different heart ventricles. This is possible, because all sub-volumes are indexed according to their semantic content and are stored in an indexed manner in the database.

After having computed the set of sub-volumes relating to the respective query, the sub-volumes are merged in order to generate a query-specific volume. The query-specific volume is a newly generated volume which specifically refers to the input query and in the example case above to all three-dimensional images with respect to the heart. In this respect, it has to be pointed out that the query-specific volume does not refer to an image of a specific patient, but may refer to a plurality of patient's images, which all consist of the anatomical structure, the input query refers to. The query-specific volume is an artificial or virtual volume, based on a plurality of different patient images. The query-specific volume may, thus, comprise images from different acquisition times, modalities and/or patients. The computed and newly generated query-specific volume may be stored and/or forwarded to other computer instances for further processing.

According to an example embodiment, the step of computing comprises a validity check. The validity check serves to check whether the position of the computed result (set of sub-volumes) in fact is within a range, where the anatomical feature or structure the query refers to may be found in the body. For example, if the query relates to an anatomical structure of the patient's head, the computed sub-volumes have to part of the head. If, however, the computed sub-volumes are positioned in the feet of the patient, the validity check may output an error. Thus, the validity check has the function that the computed set of sub-volumes is analyzed with respect to its position in the patient's body in general and whether the anatomical structure indeed may be found in the computed sub-volumes.

According to a first embodiment, the query-specific volume is generated as a kind of collage, wherein all the different results of the query-based sub-images or sub-volumes are displayed as a two-dimensional representation and merged to generate one common image with a plurality of sub-images, so that a first sub-image may be displayed adjacent to a second one (for example as an image gallery by thumbnail images). According to a second embodiment, at least some of the sub-volumes are also displayed as several two-dimension representation or slices and may be displayed in an overlay manner. In a third embodiment the query-based volume is not displayed as a stack of 2D-images, but as a 3D volume in a parallel manner (several 3D volumes being displayed in parallel on the monitor) or sequentially (the volumes are displayed one after the other).

The system comprises a plurality of computer-based instances. The image archive is a storage for storing a plurality of medical volumes. The image archive may consist of a sub-volume archive for storing the indexed sub-volumes. However, it is also possible to provide the sub-volume archive as a separate instance.

The workflow unit is adapted to receive a notification in case of a new image is stored in the image archive and based on the reception of such a notification, the workflow unit is adapted to start a landmark detector unit.

The landmark detector unit is adapted to automatically detect landmarks in an image by accessing a background knowledge database. The background knowledge database serves to understand the anatomical content or meaning of the landmarks detected.

The registration unit serves for matching the detected landmarks as a result of the landmark detector with at least one atlas image or with at least one multiple atlas image.

The split and merge unit serves for splitting the three-dimensional medical volume into three-dimensional sub-volumes with configurable physical size and for merging selected indexed sub-volumes to create a query-specific volume enclosing or covering the anatomical structure which the query refers to.

The knowledge repository with the background knowledge database and a meta image index database serve for storing a relation of index data and three-dimensional volume data.

The graphical search interface is adapted for inputting a query and for displaying a result with a plurality of selected sub-volumes of different images, wherein all of the selected sub-volumes relate to the anatomical structure, the query refers to.

The query expansion unit is adapted to expand the input query to anatomical features by accessing the background knowledge database.

The search engine is adapted to parse the query and to map it to at least one ontological data entry.

The sub-volume selector is adapted to select and aggregate all indexed sub-volumes which relate to the query and to merge the selected sub-volumes to generate a query-specific volume to be displayed as result.

According to an example embodiment, the volume and/or the indexed sub-volumes may be partitioned or segmented in volume cells of corresponding size. The "partitioning" may be executed by way of a grid structure or cube structure, which is overlaid over the volume in order to generate smaller volume cells of corresponding or different size. This has the advantage that search efficiency may be enhanced. Thus, the input image is tessellated, i.e. it is split into multiple three-dimensional cells enclosing a larger cluster of the original image voxels. The cells are stored in a sub-image archive. The size of the cells is configurable. The size of the cells may be configured according to a length unit (cm/mm) and independent of the acquisition parameters. The acquisition parameters determine the acquisition's pixel size (resolution). Today there are image acquisition devices such as Computed Tomography scanners which deliver images with a resolution of 0.3 mm×0.3 mm×1 mm. But the cell size used in the system according to the invention is less technically motivated than rather from the perspective of medicine (and medical use). Usually, a typical finding found by a reading physician is rather in the size range of centimeters. Therefore it is more efficient to store cells in anatomically reasonable sizes. Preferably, the cells are of corresponding size but the size is configurable within the system. The dimension or size of the resulting sub-volume cells is defined by aggregating a plurality of cells, which in turn is dependent on the content of the query and the respective anatomical structure.

The atlas registration is used to normalize the patient coordinate system such that table position of the acquisition device and patient size can be ignored in the following processing steps. The aim is to map similar anatomical structures to the same spatial image region (independent of the fact whether the image relates to a small or a large/tall patient). Hence, with this normalization, e.g., every heart center is located at the normalized coordinates of the heart.

According to an example embodiment, not only one atlas image is used, but a plurality of different atlas images. Subsequently, the atlas image is selected, which best corresponds to the acquired and reconstructed or provided medical three-dimensional image. For example atlas images may be provided for small/large/tall patients, for thick/thin patients and the like so that for a specific size, form and other parameters of the patients the best fitting atlas image may be selected which is used for the step of matching. With this feature, the quality of the query-based anatomical structure extraction may be enhanced.

In general terms, the methods and system according to the invention provide a fast mechanism for searching and extracting three-dimensional regions of interests in image archives, which are storing a plurality of medical volume data. The method and system are knowledge-based, i.e. the query input is analyzed on a semantic level so that it is possible to understand the image content and the user's input query. This enables the system to provide a search result automatically and to extremely increase the position and recall of the search result. Optionally, the images are automatically tagged (labeled or annotated), so that no user interaction at all is needed. Up to now and according to state of the art systems, all volume images have to be downloaded from an archive, so that the user manually has to select interesting regions of interest. This known approach leads to high execution times and very high network consumptions, as it is necessary to download all the volume data (although only a very specific part of the volume data is necessary to answer the respective query). A major advantage of the present invention, thus, has to be seen in that the transferred data volume may be reduced significantly. Further, network transmission capacity may be reduced. Moreover, it is no longer necessary to download all the volume data. Only the selected merged and computed sub-volumes are used to generate a query-specific volume which is to be transferred and displayed as query-specific volume. The query-specific volume is significantly smaller than the volumes of the provided medical three-dimensional images. For near real time selecting and returning a query-specific volume as result (downloading only a portion of the volume), a vast amount of three-dimensional regions of interests from the image archive back to the user, the backend infrastructure according to an embodiment of this invention makes use of a cell raster approach with tessellated images.

Further, at least one embodiment of the invention enables to query three-dimensional regions of interests (as anatomical structures) in a plurality of three-dimensional volumes (stored in an image archive). The input data is a textual query and the output data mainly refer to a newly generated query-specific volume, which is to be displayed on a monitor or which may be forwarded to other computer instances for further processing. The output, thus, refers to a three-dimensional query-specific volume. The query-specific volume is a set of merged computed sub-volumes which do refer to the anatomical structure of the query. This has a major advantage as it is possible to extract and select sub-volumes of a plurality of different volumes.

According to an aspect of at least one embodiment of the present invention, it is possible to use the methods and system for the purpose of supporting a physician in examining and diagnosing a patient. For example, if the physician inputs the query "show breast tumor in computer tomography", he receives the result in a query-specific volume which covers all three-dimensional image portions which cover breast tumors from a plurality of different patients and/or from a plurality of acquisition times and/or in a plurality of different cancer stages etc. Therefore, the physician is provided with a plurality of different breast tumors so that he may find a diagnosis more easily. In this respect, it has to be mentioned that the query-specific volume which is provided to the user does not necessitate downloading the respective volumes in which the sub-volumes are included. This is based on the fact, that all sub-volumes are indexed separately, so that it is possible to access a sub-volume in the database directly without the necessity to download the volume as a whole.

According to another aspect, at least one embodiment of the invention may be implemented in a computer program being loadable in a memory of a computer, wherein the computer program is adapted to carry out the steps of at least one embodiment of the methods as mentioned above.

Figure 1:
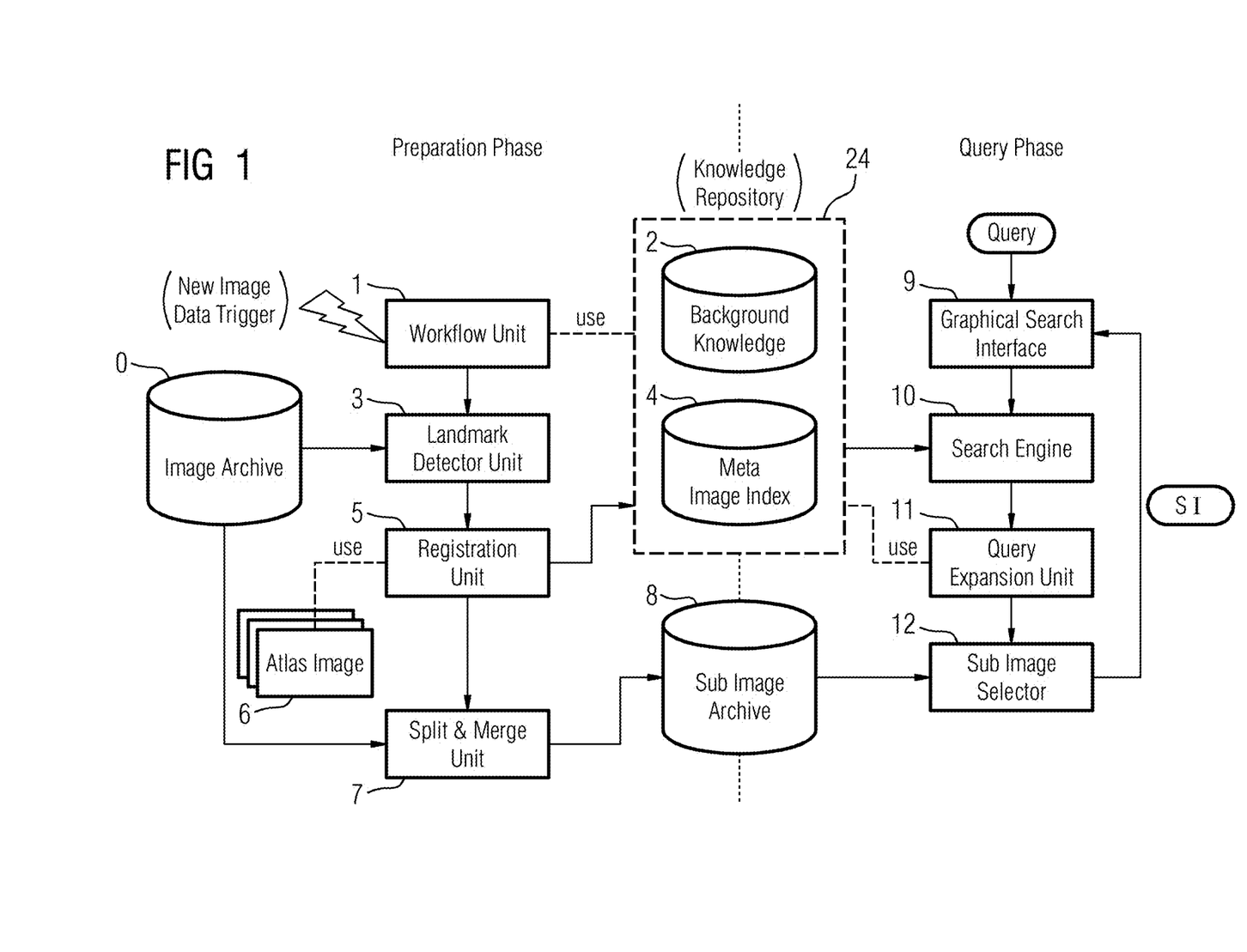
FIG. 1 is a schematic overview and block diagram of the system according to an example embodiment of the invention.

FIG. 1 shows a system for feature-based extraction of medical sub-volumes of a plurality of medical volumes. The system, thus, refers to searching anatomical structures in three-dimensional volumes, which are identified by a textual query. The main input data refer to a textual query (for example: "show lung cancer", "show examples of breast tumors" etc.). The output mainly refers to a newly generated query-specific volume. The volume comprises only those sub-volumes inclosing the anatomical structure the input query refers to (the bounding volume)

As can be seen in FIG. 1, the system works in two separate phases: a preparation phase, which is depicted on the left hand side in FIG. 1 and a query phase which is a subsequent phase of the preparation phase and which is depicted in FIG. 1 on the right hand side. The query phase may be executed at any time after the preparation phase has been ended.

A workflow unit, which in the figure is depicted with reference numeral 1, receives a notification of an image archive 0, in which three-dimensional medical volume data are stored. Generally, the preparation phase may be triggered by events of the image archive 0, for example by way of a respective notification. The notification may refer to the fact that new medical images are available in the image archive 0. The "new image data trigger" is depicted in FIG. 1 with the arrow coming from the left side to the workflow unit 1. After the workflow unit 1 has received this trigger event (e.g. a notification), it starts a landmark detection. The landmark detection is an automatic processing by a landmark detector unit 3. Several landmarks are used. For example 20 landmarks are enough for the system to work in high quality. It is important that enough representative landmarks in every body part or portion are present (for example in head, neck, thorax, abdomen, pelvis, extremities etc.). The workflow unit 1 uses a background knowledge database 2 to analyze the anatomical meaning (semantic content) of the landmarks detected by the landmark detector unit 3. The detected landmarks are stored in a meta image index database 4, which is adapted to store meta image indexes. In a registration unit 5 the landmark detection result is taken and registered with an atlas image 6 (or with a plurality of atlas images 6). The at least one atlas image 6 is a very detailed and segmented and indexed volume with indexed sub-volumes. The atlas image may be created manually or by way of automated procedures. The atlas image comprises landmarks (for example: head, neck, thorax etc.). It is possible to execute a mapping between the provided image (the new image in the image archive 0) and the atlas image 6. In this respect, registration algorithms may be used. In particular for example the thin-plate splines landmark registration approach may be used by the registration unit 5.

Thus, as soon as a new image is stored in the image archive 0, the image is preprocessed, so that all sub-volumes, shown in the new image, are indexed separately and all the indexed sub-volumes are stored in a sub-image archive 8 which is also depicted in FIG. 1. The result of the preparation phase refers to storing indexed sub-volumes in the sub-image archive 8.

Subsequently, it is possible to execute the query phase. In the query phase the user uses a graphical search interface 9 to input a query string, particularly a textual string, e.g. "give me all regions of interest with the heart". A search engine 10 parses the query input and maps it to semantic index information (semantic concepts). Together with index information from the meta image index (database) 4 the concepts are forwarded to a query expansion unit 11. The task of the query expansion unit 11 is to expand the input concept into related meaningful concepts by the use of a background knowledge database 2. Resulting multiple sub-queries are parsed to a sub-image selector 12, which selects all the matching sub-image regions in the sub-image archive 8, consisting of a set of three-dimensional (volume) cells. The result is then returned from the sub-image selector 12 to graphical search interface 9 and adequately visualized to the user or provided for download. Accordingly, only a small fraction of volume data is to be provided for download. Only the relevant regions of interest of a plurality of volume data image files are to be presented as query-specific volume. It is no longer necessary to download all the volume data files, which cover the anatomical structure the query refers to (by contrast: this was necessary in state of the art systems).

The background knowledge database 2 and the meta image index database 4 may be provided as knowledge repository 24.

Figure 2:
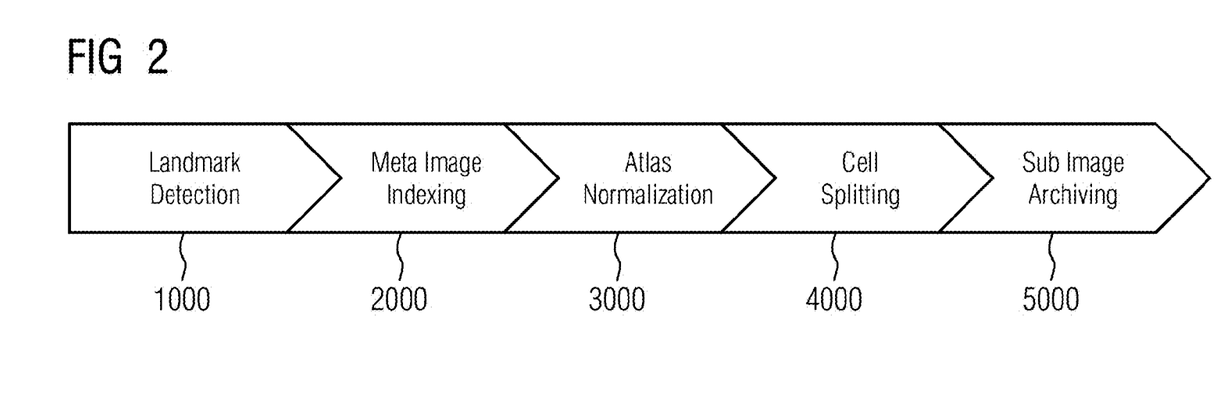
FIG. 2 is an example flow chart of a preparation process according to an aspect of an example embodiment of the invention.

FIG. 2 shows an example of a preparation process. First, discriminant landmarks are detected which span a landmark coordinate system in the input image (volume image). This is depicted in FIG. 2 with reference numeral 1000. The landmarks as well as the image boundaries expressed in landmark coordinates are then stored as index. The meta image indexing is referred to in FIG. 2 with reference numeral 2000. This enables fast selection of image candidates which are within the queried body range. For semantically annotating a vast amount of anatomical structures in the three-dimensional input image, the system associates it with an atlas image 6 by using a landmark-based registration approach. This atlas normalization is depicted in FIG. 2 with reference numeral 3000. The result is a mapping between locations of anatomical structures in the atlas coordinate space to the related ones in the input coordinate space (the input volume). For search efficiency reasons the input image is tessellated, i.e., split into multiple three-dimensional cells inclosing larger clusters of the original image voxels. The cell splitting is depicted in FIG. 2 with reference numeral 4000. Subsequently, the cells are stored in a sub-image archive 8, which is depicted in FIG. 2 with reference numeral 5000.

Figure 3:
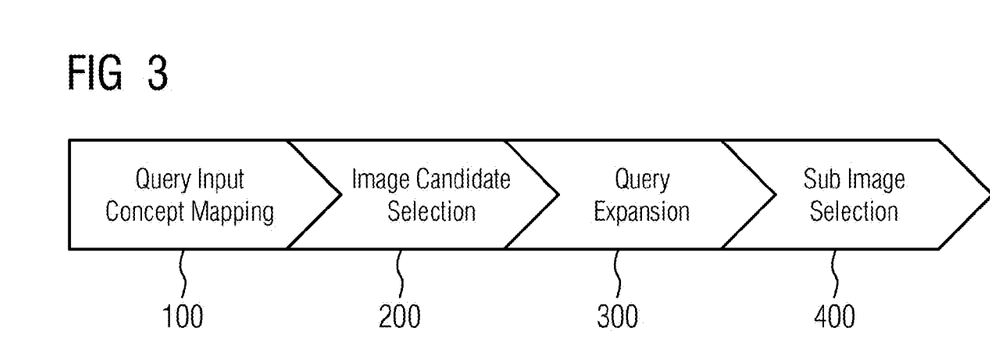
FIG. 3 is an example flow chart of a query process according to an aspect of an example embodiment of the invention.

The query process is illustrated in FIG. 3 in more detail. First, the query input is mapped to semantic concepts in step 100 by the use of the medical background knowledge database 2. This may be implemented as an ontology. Subsequently, in step 200 the image candidates are selected using the meta index information in database 4. The image candidate selection is depicted in FIG. 3 with reference numeral 200. The input semantic concept is expanded using again the medical background knowledge database 2 and is passed to the sub-image selection step: its responsibility is to collect and aggregate volume cells to sub-image regions or sub-volumes fully covering the queried anatomical structure in a plurality of images. The query expansion is depicted with reference numeral 300 in FIG. 3. The size of the selected image sub-volumes depends on the anatomical structure itself: A table created by an expert maps concepts to object sizes. Since for example the average male heart is about 12 cm×9 cm×6 cm, hence, the system extracts a region of interest at least of this size. Thus, the size of the sub-volumes is separately defined in each case and is dependent on the query the user inputs. Thus, for example, the size of the sub-volumes for the query "finger tip" differs from the size of the sub-volumes, referring to the query "liver", because the liver has another (usually bigger) size than a finger tip. Sub-volume selection is depicted in FIG. 3 with reference numeral 400. The size of the sub-volume is defined individually and dependent on the query.

Figure 4:
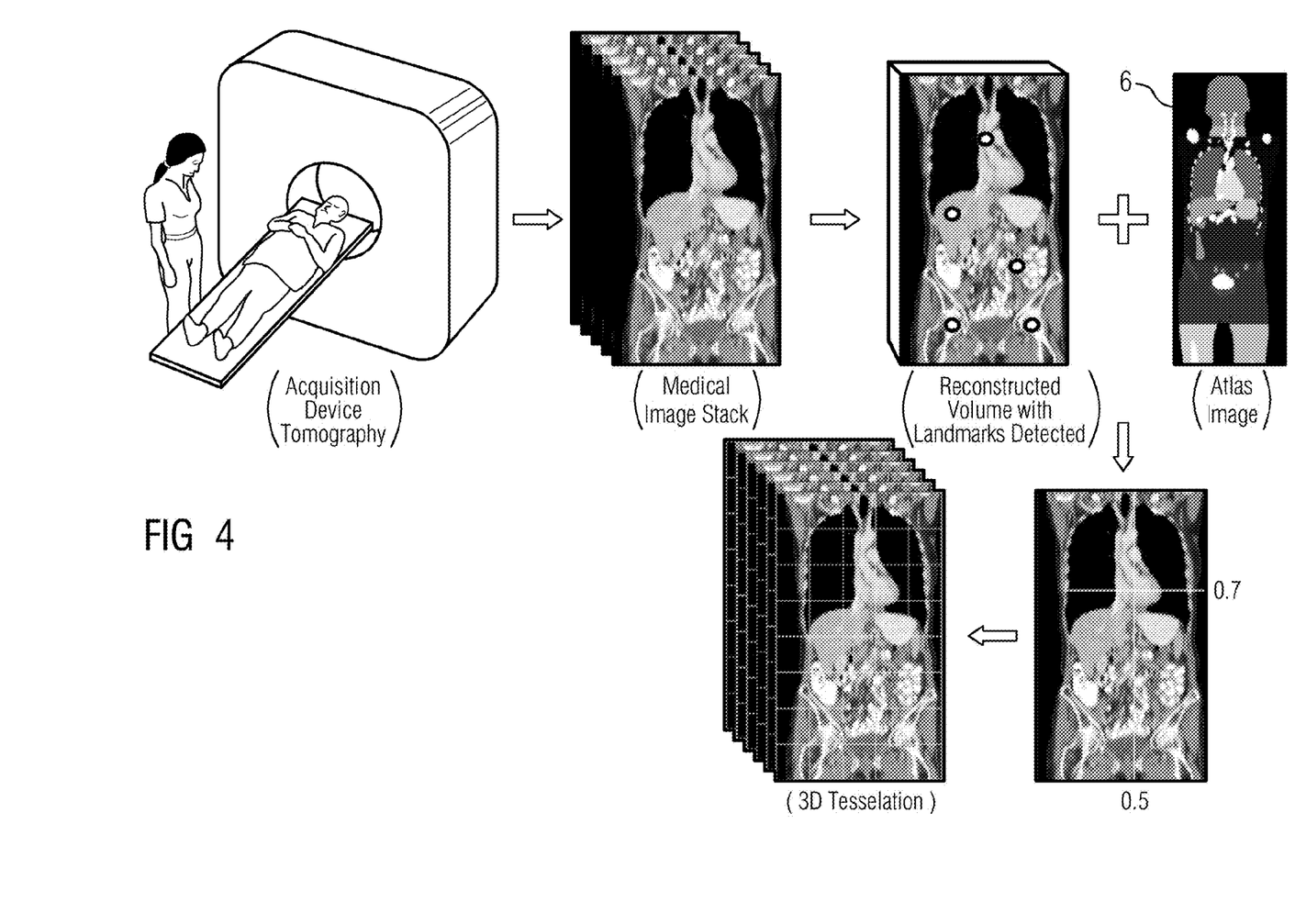
FIG. 4 is an example preprocessing workflow shown in a schematic manner.

FIG. 4 refers to an example of a preprocessing workflow. The workflow is described from left to right and in the second line from right to left according to the arrows in FIG. 4. First, the image is acquired via an acquisition device (for example a tomography apparatus). After this, a volume is reconstructed and provided as medical image stack. After this, landmarks are detected in the reconstructed volumes. In FIG. 4 this may be seen in the encircled rings, depicted in the center of the respective anatomical structure. Subsequently, a landmark-based registration with at least one atlas image 6 is accomplished. This results in an image with normalized coordinates, ignoring image acquisition parameters and body parts acquired. On the right side of the lower part in FIG. 4 the image is, then, tessellated or split into isometric three-dimensional cells (volume cells). All the acquired parameters and all the indexed sub-volumes are stored in the knowledge repository 24. The step of 3D tessellation or splitting is depicted in FIG. 4 on the left hand side on the lower part in FIG. 4.

Figure 5:
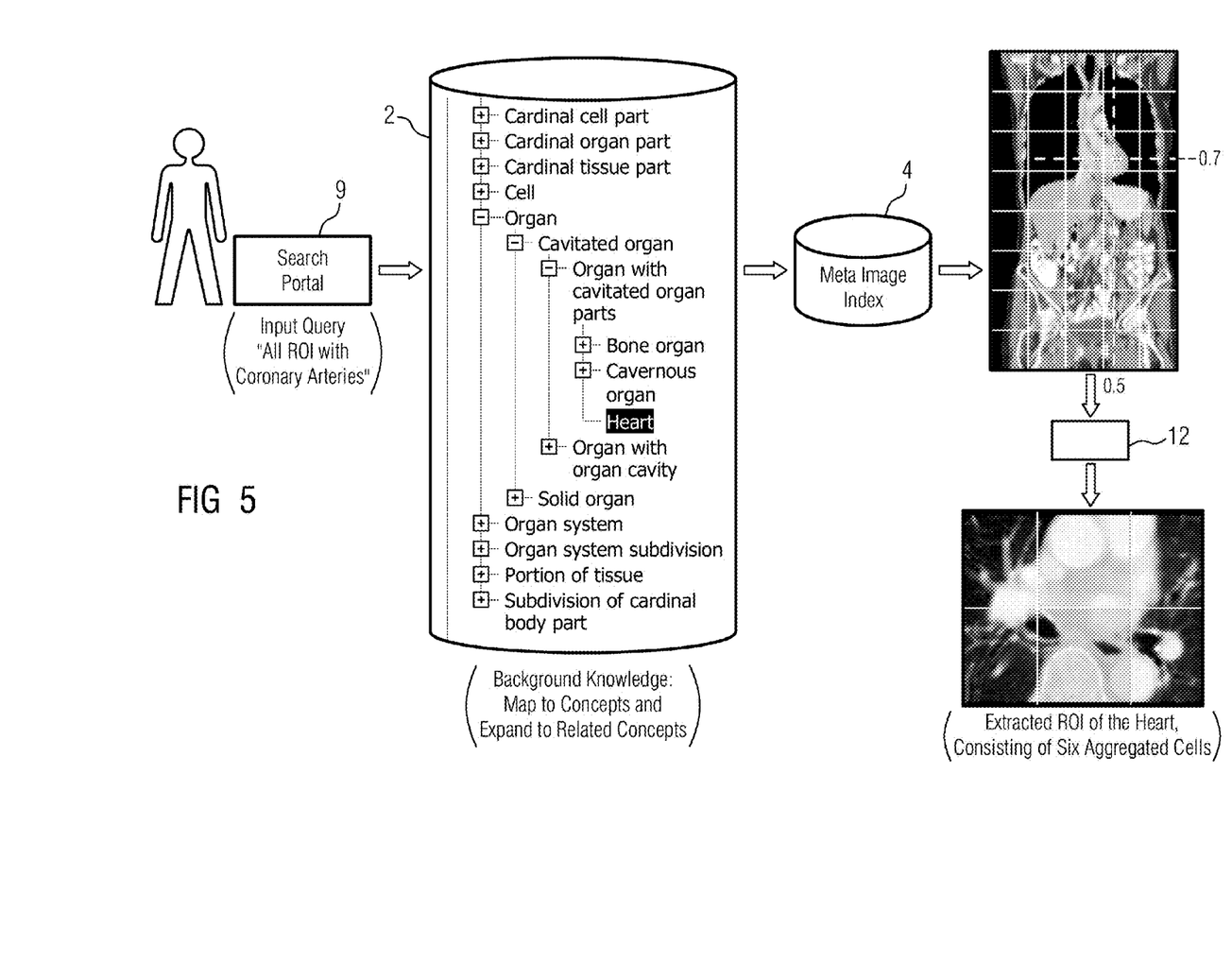
FIG. 5 is an example of a query process according to an embodiment of the present invention and FIG. 6 is an example of a tessellation and splitting process according to an embodiment of the present invention.

FIG. 5 shows an example query process. The user inputs the query as text via the graphical search interface 9, which may be referred to as "search portal". For example the user may input: "all regions of interest with coronary arteries". The system then automatically parses and maps this query text to ontological concepts. This may be done by accessing the background knowledge repository 24, in order to map to concepts and expand to related concepts. The concepts are expanded to related concepts. This is done by traversing edges in the ontology, which is a kind of graph consisting of nodes representing an entity and edges representing the relation between two entities. In the selected ontologies, for example, the subclassOf and regionalPartOf relations are used, but the invention is not limited to those. By the use of the meta image index 4, the appropriate sub-volume cells are computed, which cover the anatomical structures of the concepts in the image. Subsequently, the region of interest (i.e. the respective merged sub-volumes) is generated by accessing the sub-image selector 12. The sub-volumes are extracted by aggregating in this case six cells to the resulting sub-volume, as can be seen in FIG. 5 by the last image, split into six cells. In this respect, it has to be noted that all the image examples, depicted in the figures, refer to three-dimensional images and only are represented as a two-dimensional structure. However, the image itself refers to a three-dimensional structure.

Figure 6:
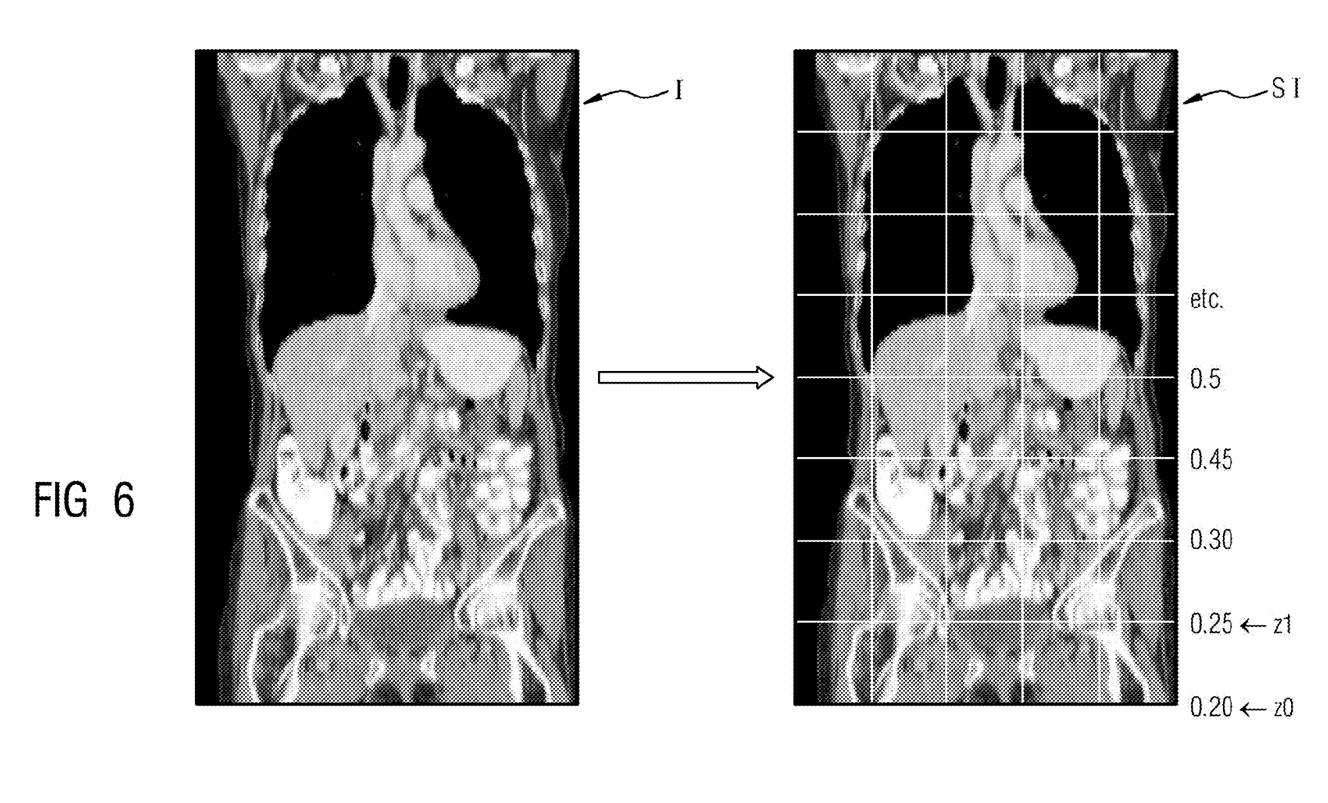

FIG. 6 shows an example of a tessellation process or the splitting into sub-volumes SI. According to an embodiment, the acquired three-dimensional image I of a patient is shown on the left hand side in FIG. 6. The volume I is rasterized into sub-volumes SI or volume cells, which are depicted on the right hand side in FIG. 6. The image example in FIG. 6 refers to upper abdomen structures. Instead of storing the whole image I as one instance in the image archive, all the different sub-volumes SI are stored in the sub-image archive 8. Each sub-volume SI is indexed separately with normalized coordinates and stored in the image archive 8. Additionally, all labels of the atlas image, which are also covered by this sub-volume SI, are also stored in the index, too.

The example embodiments are to be considered in all respects only as illustrative and not restrictive. The scope of the invention is, therefore, indicated by the appended claims rather than by this description. All changes which come within the meaning and range of equivalency of the claims are to be embraced within their scope.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

1 workflow unit
2 background knowledge database
3 landmark detector unit
4 meta image index
5 registration unit
6 atlas image, multi atlas image
7 split and merge unit
8 sub-image archive
9 graphical search interface or search portal
10 search engine
11 query expansion unit
12 sub-image selector
0 image archive
24 knowledge repository
SI sub-volume image
I medical three-dimensional image
1000 landmark detection
2000 meta image indexing
3000 atlas normalization
4000 cell splitting
5000 sub-image archiving
100 query input concept mapping
200 image candidate selection
300 query expansion
400 sub-volume selection

What is claimed is:

1. An automatic image preprocessing method for generating sub-volumes of a plurality of three dimensional medical volumes for semantic extraction of anatomical structures, the method comprising:
providing, or acquiring and reconstructing, a medical three dimensional image as a volume, the volume including different anatomical structures or a part of an anatomical structure;
partitioning the volume by generating volume cells of corresponding size;
automatically detecting landmarks in the volume;
matching the detected landmarks with at least one atlas image to generate an indexed volume, each of the volume cells indexed according to the matching;
splitting the indexed volume into indexed sub-volumes according to atlas image data; and
storing the indexed sub-volumes in a database.

2. The method of claim 1, wherein the corresponding size of the volume cells is configurable and is specifiable in units of length, the units of length including centimeters or millimeters.

3. The method of claim 1, wherein the automatically detecting landmarks is executed iteratively by accessing a background knowledge database to generate further landmarks using the detected landmarks as an anchor structure.

4. The method of claim 1, wherein
the at least one atlas image includes multiple atlas images and
the matching includes
selecting, from a plurality of different atlas images, a conforming atlas image corresponding to the medical three dimensional image.

5. A method for query-based extraction of anatomical structures in a plurality of three dimensional medical images, the method comprising:
providing a plurality of medical volumes with indexed sub-volumes, preprocessed and indexed based upon the method of claim 1;
inputting and parsing a textual medical query, referring to an anatomical structure;
mapping the parsed textual medical query to at least one ontological data entry in an ontology database based on a meta image index;
computing a set of sub-volumes including an index matching the textual medical query, wherein the set of sub-volumes include at least a part of the anatomical structure to which the textual medical query refers;
merging the set of computed sub-volumes to generate a query-specific volume; and
displaying the query-specific volume.

6. The method of claim 5, wherein each image of the plurality of three dimensional medical images refers to at least one of different acquisition times, different acquisition modalities and different patients.

7. The method of claim 5, wherein the textual medical query is expandable to at least one of (i) infer semantically related sub-queries and (ii) suggest automatic corrections for incorrect queries.

8. The method of claim 5, further comprising:
at least one of storing and forwarding the set of computed sub-volumes to other computer instances.

9. The method of claim 5, further comprising:
performing a validity check including analyzing the computed set of sub-volumes with respect to positions in a patient's body and whether the anatomical structure is found in the computed sub-volumes.

10. The method of claim 5, wherein the method is used for automatically localizing anatomical structures in a plurality of medical volumes without loading each of the plurality of volumes separately and manually searching the anatomical structure in the volume.

11. A system for extraction of anatomical structures as medical sub-volumes of a plurality of volumes, the system comprising:
an image archive to store a plurality of medical volumes;
one or more processors configured to execute computer-readable instructions such that the one or more processors are configured to
receive a notification of a new three dimensional medical image stored as a three dimensional medical volume in the image archive, the three dimensional medical volume including at least a part of an anatomical structure,
initiate, based on the received notification, detection of landmarks in the three dimensional medical volume by accessing a background knowledge database,
match the detected landmarks with at least one atlas image to generate an indexed volume,
split the three dimensional medical volume into three dimensional sub-volumes with configurable physical size,
merge selected sub-volumes, from among the three dimensional sub-volumes, to create at least one query-specific volume including at least the part of the anatomical structure,
parse a query and map the query to at least one ontological data entry, and
expand the query to anatomical features by accessing the background knowledge database;
a memory including a knowledge repository, the knowledge repository including the background knowledge database and a meta image index database, and the knowledge repository configured to store a relation of index data and three dimensional volume data; and
a display device including a graphical search interface configured to input the query and to display a result of the query with the at least one query-specific volume including at least the part of the anatomical structure.

12. A computer program product, including a non-transitory computer readable medium storing computer readable program code to cause a computer to perform the method of claim 1, upon the program code being executed or loaded in the computer.

13. A computer program product including a non-transitory computer readable medium storing computer readable program code to cause a computer to perform the method of claim 5, upon the program code being executed or loaded in the computer.

14. The method of claim 2, wherein the size of the volume cells is configurable based on an anatomical structure to be extracted and independent of the acquisition parameters for the medical three dimensional image.

15. The system of claim 11, wherein the one or more processors are configured to execute computer-readable instructions such that the one or more processors are further configured to access the background knowledge database to generate further landmarks by using the detected landmarks as an anchor structure.

16. The system of claim 11, wherein
the at least one atlas image includes multiple atlas images; and
the matching includes selecting, from a plurality of different atlas images, a conforming atlas image corresponding to the three dimensional medical image.

17. The method of claim 6, wherein the input textual medical query is expandable to at least one of infer semantically related sub-queries and suggest automatic corrections for incorrect queries.

18. The system of claim 11, wherein the one or more processors are configured to execute the computer-readable instructions such that the one or more processors are further configured to merge sub-volumes selected by:
providing a plurality of medical volumes with indexed sub-volumes;
inputting and parsing a textual medical query referring to an anatomical structure;
mapping the parsed textual medical query to at least one ontological data entry in an ontology database by way of a meta image index;

computing a set of sub-volumes including an index matching the textual medical query, wherein the set of sub-volumes includes at least a part of the anatomical structure to which the textual medical query refers;

merging the set of sub-volumes to generate a query-specific volume; and displaying the query-specific volume.

19. A non-transitory computer readable medium including computer readable program code to cause a computer to perform the method of claim 1, upon the program code being executed or loaded in the computer.

20. A non-transitory computer readable medium including computer readable program code to cause a computer to perform the method of claim 5, upon the program code being executed or loaded in the computer.

* * * * *